United States Patent
Markovsky et al.

(10) Patent No.: US 10,247,728 B1
(45) Date of Patent: Apr. 2, 2019

(54) METHOD AND ASSAY FOR DETECTION OF RESIDUES

(71) Applicant: Charm Sciences, Inc., Lawrence, MA (US)

(72) Inventors: Robert J. Markovsky, Brentwood, NH (US); David W. Douglas, Andover, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days.

(21) Appl. No.: 15/460,594

(22) Filed: Mar. 16, 2017

Related U.S. Application Data

(60) Provisional application No. 62/309,572, filed on Mar. 17, 2016.

(51) Int. Cl.
*G01N 33/569* (2006.01)
*G01N 33/558* (2006.01)

(52) U.S. Cl.
CPC ..... *G01N 33/56938* (2013.01); *G01N 33/558* (2013.01); *G01N 2469/20* (2013.01)

(58) Field of Classification Search
CPC ............... G01N 33/56938; G01N 33/558
See application file for complete search history.

(56) References Cited

U.S. PATENT DOCUMENTS

| | | | |
|---|---|---|---|
| 5,985,675 A | 11/1999 | Chaim et al. ............ 436/514 |
| 6,319,466 B1 | 11/2001 | Markovsky et al. ........ 422/56 |
| 2004/0219690 A1* | 11/2004 | Choi .................. G01N 33/533 436/514 |
| 2009/0286692 A1* | 11/2009 | Wainwright ...... B01L 3/502723 506/9 |
| 2015/0361178 A1* | 12/2015 | Soldo ................ C07K 16/2869 435/7.94 |
| 2016/0333338 A1* | 11/2016 | Haj-Ahmad ....... C12N 15/1006 |

\* cited by examiner

*Primary Examiner* — Melanie Brown
(74) *Attorney, Agent, or Firm* — MacCord Mason PLLC

(57) ABSTRACT

Embodiments described herein include detecting an analyte in a low pH sample. Some embodiments include detection of multiple analytes in a sample utilizing a plurality of analyte binders and a control zone containing multiple control zone capture agents. In some embodiments, the multiple control zone capture agents capture a plurality of binders within one control zone.

10 Claims, 7 Drawing Sheets

METHOD AND ASSAY FOR DETECTION OF RESIDUES

This application claims the benefit of U.S. provisional application No. 62/309,572, filed Mar. 17, 2016, which is incorporated herein by reference in its entirety.

FIELD OF THE TECHNOLOGY

The present disclosure relates generally to binding assays and, more particularly, to systems, assemblies, and methods for detecting the presence of one or more analytes in a sample having a low pH.

BACKGROUND

Antibiotic residues in foods are a major food safety concern. Health issues include bacterial resistance to drugs and allergic reactions. To avoid the impact of such health issues, food is tested worldwide for antibiotics and other contaminants. One type of test method uses what is commonly known as a lateral flow test strip.

Lateral-flow test strips for detecting one or more analytes in a fluid sample may include a capture agent immobilized within a region of the test sometimes referred to as a detection zone. Detection zones can include test zones and control zones. A typical capture agent has binding affinity for a substance that may be in the mobile phase of the test strip. Lateral-flow tests in which the binding of a substance from a mobile phase to a capture agent generates a visible signal, that can be interpreted visually or using a reader, such as a spectrophotomer, are well known in the art. Examples of such devices are described in U.S. Pat. No. 5,985,675, issued Nov. 16, 1999; and U.S. Pat. No. 6,319,466, issued Nov. 20, 2001, and U.S. patent application Ser. No. 10/289,089, filed Nov. 6, 2002 (based on U.S. Provisional Application 60/332,877, filed Nov. 6, 2001) all of which are incorporated herein by reference.

Lateral-flow tests are widely used in the food products industry. One application is in testing dairy products. However, other fluids often contain characteristics that limit, or even prohibit, efficient use of traditional lateral-flow tests. For example, citrus juices and oils may not be compatible with conventional lateral-flow tests because of their low pH. Yet, these, and other low pH fluids, are subject to regulation by the United States Food and Drug Administration (FDA). For example, citrus juices are commonly treated with antibiotics to prevent citrus cankers and other fungal infections. While the FDA has approved certain antibiotics, such as oxytetracycline and streptomycin, the FDA has prohibited others, such as penicillin, and requires that citrus juices and oils be tested for unsafe levels of certain beta-lactam antibiotics. It is desirable, therefore, to provide juice-testing personnel with a user-friendly test that can be analyzed with or without a reader and can detect multiple beta-lactams, such as penicillin, when present at or above a threshold level.

Therefore, Applicants desire detection of residues in a low pH sample without the drawbacks presented by the traditional systems and methods.

SUMMARY

In accordance with the present disclosure, test strips and systems are provided for the analysis in a sample. This disclosure provides improved systems, devices, assemblies, and methods that are convenient, efficient, and safe for the user, particularly when used to detect the presence or absence of an analyte in a low pH sample.

In one embodiment, a method for detecting one or more analytes in a solution includes applying a binder to a test strip, the binder configured for generating a detectable signal and capable of combining with the analyte to form a binder-analyte complex; immobilizing, within one or more test zones of the test strip, at least one test zone capture agents capable of capturing the binder; immobilizing, within a control zone of the test strip, at least one control zone capture agent adapted for capturing the binder and the binder-analyte complex; providing a sample having a pH less than 7; raising the pH of the sample by diluting with a buffer to form the solution; and adding the solution to the test strip; and wherein one or more analytes in the solution, when present, are adapted to combine with one or more of the binders to form the binder-analyte complex and wherein a comparison of the signal in the control zone to the signal in the test zone provides a test result. In some examples, the sample is a citrus juice. The pH of the sample may be between about 2 and about 5.

In another embodiment, an assembly for detecting an analyte in a solution, the assembly includes (a) a buffer comprising a mixture of bovine serum albumin and sodium bicarbonate, said buffer added to a citrus juice sample and increasing a pH of the citrus juice sample, wherein the combination of the citrus juice sample and the buffer forms the solution; (b) a binder configured for generating a detectable signal, wherein the binder can combine with an analyte from the solution to form a binder-analyte complex; and (c) a test strip configured to allow a test solution to flow, wherein the test solution contains either or both a binder and a binder-analyte complex, the test strip comprising: (i) a test zone having immobilized thereon a test zone capture agent that, when the binder has not formed a binder-analyte complex, captures the binder, (ii) a control zone having at least one control zone capture agent adapted to capture the binder, whether or not the binder has formed a binder-analyte complex, and wherein capture of the binder at either the test zone or control zone results in a detectable signal and wherein a greater signal in the control zone as compared to the test zone indicates a positive result.

Another embodiment of the disclosures is a lateral flow assay system for detecting one or more analytes in a solution, the system comprising: (a) a buffer configured to increase the pH of a low pH sample to an optimal pH, wherein the combination of the low pH sample and the buffer forms the solution; (b) a binder configured for generating a detectable signal, wherein the binder being adapted to combine with an analyte from the solution to form a binder-analyte complex; and (c) a test strip configured to allow a test solution to flow, wherein the test solution contains either or both a binder and a binder-analyte complex, the test strip comprising: (i) a test zone having immobilized thereon a test zone capture agent that, when the binder has not formed a binder-analyte complex, captures the binder, (ii) a control zone having at least one control zone capture agent adapted to capture the binder, whether or not the binder has formed a binder-analyte complex, and wherein capture of the binder at either the test zone or control zone results in a detectable signal and wherein a greater signal in the control zone as compared to the test zone indicates a positive result.

In some examples, the low pH sample has a pH less than about 7. The low pH sample may have a pH between about 2 and about 5, for instance the low pH sample may have a pH of about 3.

In particular examples, the low pH sample is a citrus juice. For instance, the citrus may include lemon juice, lime juice, grapefruit juice, orange juice, and the like. The buffer may comprise a mixture of a carrier protein and a base. The carrier protein may comprise bovine serum albumin. The base may comprise sodium bicarbonate. The sodium bicarbonate may comprise about 0.7M. The optimal pH may be about 7.

In some examples, the control zone capture agents have affinity to each other. For instance, the control zone capture agent may comprise an antibody. The control zone capture agent may comprise an antibody binding protein. The antibody binding protein may comprise protein A. At least one of the control zone capture agents may comprise an antibody and another comprises protein A. The binder may comprise an antibody. The binder may comprise a multianalyte binder derived from a bacteria. The control zone capture agent may be immobilized on the control zone through attachment to a carrier protein. The carrier protein may comprise bovine serum albumin. One of the control zone capture agents may comprise an antibody binding protein and another control zone capture agent is an antibody to which the antibody binding protein has affinity, and wherein the antibody is applied to the test strip with the binder, and flows, either with the binder or attached to the binder, to the control zone. The binder may comprise a beta-lactam binder and wherein one of the control zone capture agents comprises an antibody to the beta-lactam binder. The binder may comprise a beta-lactam binder and wherein one of the control zone capture agents comprises an antibody to the beta-lactam binder. One of the plurality of binders may comprise a multianalyte binder with binding affinity for beta-lactam antibiotics. The multianalyte binder may comprise a beta-lactam binder from *Geobacillus stearothermophilus*. One of the control zone capture agents may comprise an antibody to the multianalyte beta-lactam binder. One of the plurality of binders may comprise an antibody. The antibody may comprise an antibody to penicillin. One or more unlabeled binders unlabeled binders may reduce test sensitivity relative to the analyte to which the unlabeled binder has affinity.

In particular examples, at least two of the control zone capture agents may be antibodies. At least two central control zone capture agents may be antibodies and wherein each of the antibodies may have affinity to a different species of animal of binder. One of the control zone capture agents comprises a polyclonal antibody and the other may comprise a monoclonal antibody. Each of the binders may comprise an antibody from a different species of animal and at least one of the control zone capture agents comprises an antibody to one of those different species. At least one of the control zone capture agents may comprise an antibody binding protein. The antibody binding protein may comprise protein A.

In some embodiments, detection of one or more contaminants in a low pH sample is accomplished by diluting with a buffer to optimize the pH of the sample, wherein the optimal pH for the sample may be about 7. For example, the buffer may comprise a mixture of a carrier protein and a base. The carrier protein may be bovine serum albumin in one example. The base may be a weak base, such as sodium bicarbonate. In one example, the concentration of sodium bicarbonate within the buffer is about 0.7M.

Antigens, haptens and their antibodies, hormones, vitamins, drugs, metabolites and their receptors and binding materials, fungicides, herbicides, pesticides, plant, animal and microbial toxins, may be determinable using the present methods and apparatuses. Other analytes that may be determinable by the disclosed methods and apparatuses include antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin and toxins, such as mycotoxins, such as aflatoxin and vomitoxin and drugs of abuse, such as opioids and the like, as well as the metabolites thereof.

The test can include one or multiple binders each with binding affinity for one or more analytes. The test can also include a test zone capture agent and one or more control zone capture agents with binding affinity for the binders. In an example, two control zone capture agents are used each with affinity to a different binder. In another example, two control zone capture agents are used and the two control zone capture agents also have binding affinity to each other.

An example described herein is a test for detection of beta-lactam antibiotics, including test strips sensitive to penicillin G, amoxicillin, ampicillin, ceftiofur, cephapirin and penicillin with sensitivity to each at or below safe level. Such a test can include a binder for beta-lactam antibiotics, for example a beta-lactam binding protein derived from *Geobacillus stearothermophilus* (sometimes referred to as *Bacillus stearothermophilus*) ("B.st.") with affinity to multiple beta-lactams including the target beta-lactams ("the BL binder"). Generally binders with affinity to multiple drugs are hereinafter referred to as "multianalyte binders".

The test can also include a binder with greater specificity for a particular analyte as compared to a multianalyte binder, hereinafter referred to as a "specific binder", for example an antibody to an antibiotic such as penicillin ("penicillin binder") to which the multianalyte binder, such as the BL binder, may not have adequate sensitivity. In such a test, a test zone can contain a capture agent for the binder, for example representative antibiotics. When two binders are used, such as a multianalyte binder and a specific binder, a detection zone can include capture agents for both, for example capture agents immobilized in separate test zones. Immobilization can be through use of a carrier protein, such as BSA.

The test can also utilize two or more binders having sensitivity for unrelated analytes such as different families of antibiotics or toxins.

A control zone can be used for comparison to the one or more test zones or as a signal that the test functioned properly and is complete. A control zone can also include a capture agent. In an example, one of the control zone capture agents includes an antibody binding protein such as protein A, protein G or protein AG or recombinant forms of the same. In another example, one of the control zone capture agents includes an antibody, for example an antibody to a multianalyte binder immobilized on the control zone prior to testing. It is also possible that an antibody to a multianalyte beta lactam binder is not immobilized in the control zone and is instead combined with a beta lactam binder prior to testing and flows to the control zone for capture. In such an example, there is a single capture agent immobilized on the control zone prior to testing which can be an antibody binding protein.

When the control zone capture agents include an antibody binding protein, and an antibody, the capture agents may have affinity to each other, and, therefore, if combined, may have binding to each other. The control zone capture agents need not, however, have affinity to each other. For example, the control zone capture agents can include a variety of antibodies, receptors, binding proteins and the like, each with affinity to at least one of the analyte binders. Generally, however, when multiple test zones are employed, it is preferable to have a control zone be used for comparison to more than one test zone. In that way, one control zone can be used to compare to more than one test zone, thereby simplifying test result interpretation. For example, if there are two test zones one control zone can be used, or if there are four test zones then two control zones can be used.

In some embodiments one test zone and one control zone are used to capture one labeled binder, the control zone includes multiple capture agents, each with different affinity to a binder, such as each with affinity to different parts of the binder.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawing, in which.

DESCRIPTION OF EMBODIMENTS

Figure 1:
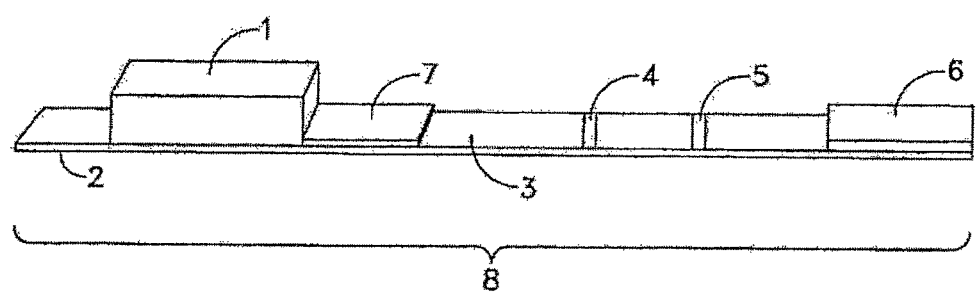
FIG. 1 is a side view of an embodiment having a test zone and a control zone.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms. Referring now to the drawings in general, it will be understood that the illustrations are for the purpose of describing embodiments of the disclosure and are not intended to limit the disclosure or any inventions thereto. Often, low pH substances, such as orange juice, have one or more analytes that may be detected as generally shown and described herein. To detect an analyte a binder for the analyte can be employed, for instance the binder may be a binding protein, such as an enzyme, antibody, receptor or other substance, capable of binding to the analyte to form an analyte-binder complex. The binder, or analyte-binder complex, may be detected through various methods shown and described herein, including labeling the binder, and, therefore, the resulting complex, with a visible label, such as a gold particle, and capturing the labeled complex with a capture agent. Herein the various embodiments provide unexpected advantages of detecting a variety of analytes, antibiotics, and the like, including, but not limited to, oxytetracycline, or similar antibiotics, and streptomycin, or similar antibiotics, as understood by those skilled in the art having the benefit of this disclosure.

Figure 2:
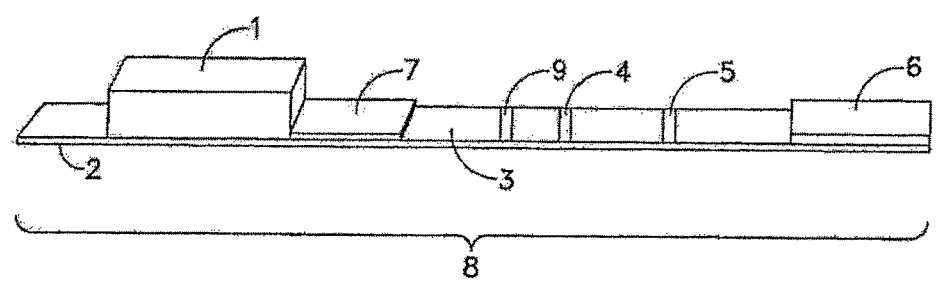
FIG. 2 is a side view of an embodiment having two test zones and a control zone.

FIG. 1 illustrates one example of a test strip apparatus 8, comprised of nitrocellulose membrane 3 and a binder application area 7 onto which the labeled binders can be added. The binder application area can be, for example, POREX® (POREX is a registered trademark of Porex Technologies Corp, Georgia USA), attached to solid support 2. If a sample pad 1 is used, the low pH sample is contacted to sample pad 1. Alternatively, the low pH sample can be applied directly to the binder application area 7. If a sample pad 7 is used, sample flows from sample pad 1 to the sample application area 7 containing, in an example, labeled specific binder and labeled multianalyte binder. Labeled specific binder and labeled multianalyte binder will bind analyte from the sample and flow along the nitrocellulose membrane 3 to test zone 4. A portion of labeled specific binder and labeled multianalyte binder, unbound by sample analyte, will be captured at the related test zone. Remaining labeled binder, whether or not bound by sample analyte, will flow to, and can bind to, control zone 5. Some labeled binder may also flow past the control zone and into the disposal pad 6. A stronger signal in the control zone as compared to the test zone is a positive result. A weaker signal in the control zone as compared to the test zone is a negative result. FIG. 2 shows another embodiment of test strip apparatus 8 further including a second test zone 9.

Prior to application to sample pad 1, the pH of a sample may need to be optimized. For example, in cases where the sample has a pH less than 7, a buffer is used to increase the pH to the assay's optimal level. Samples, such as those taken from citrus juices, may have a pH anywhere between about 2 and about 5. Those of ordinary skill in the art having the benefit of this disclosure will recognize additional sample and application uses. Typically, the buffer may comprise a mixture of a carrier protein and a base. The base may be a weak base such as sodium bicarbonate. Bovine serum albumin may be a carrier protein used within the buffer. The low pH sample may have its pH optimized by combining the buffer and low pH sample (ex: a 1:1 dilution ratio) prior to applying the sample onto sample pad 1. In one embodiment, the optimal level is typically a pH around 7, but may vary in other examples depending on assay components. Once the buffer is added, the sample may then be applied to the test strip or the like.

Figure 3:
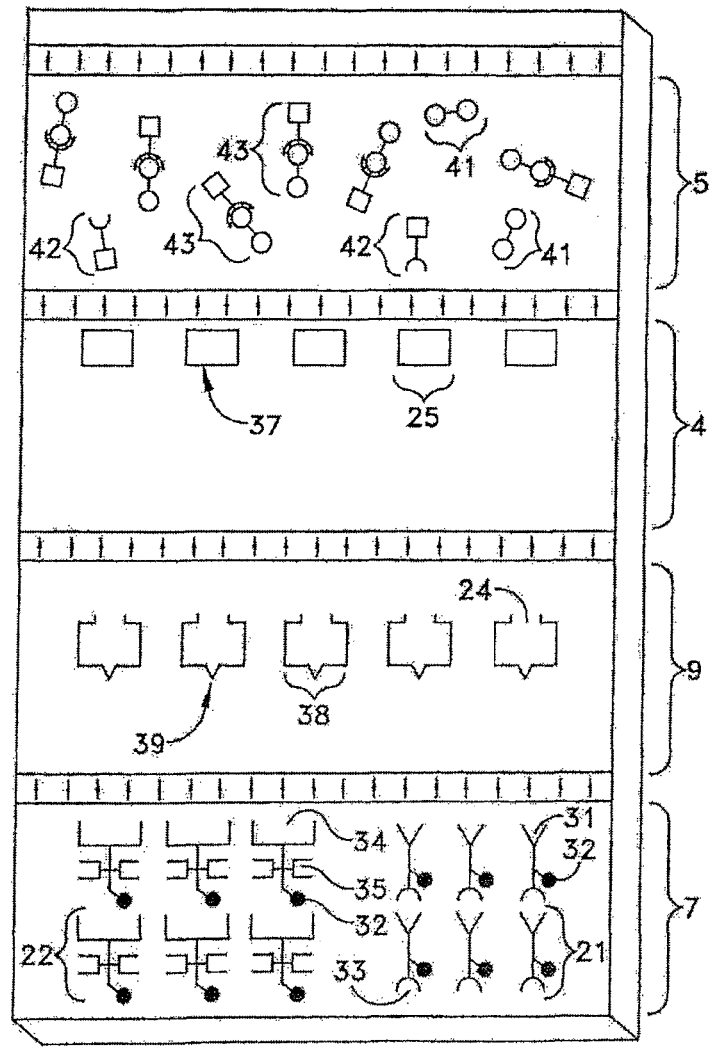
FIG. 3 is a schematic view of the arrangement of test components on the test strip prior to application of sample.

FIG. 3 shows one example of test strip components of the embodiment shown in FIG. 2 prior to application of sample solution. The arrows indicate the direction of sample flow from the binder application area 7. Not shown is a sample pad 1 or other test solution application area that may precede the binder application area 7. The binders in the application area are, in this example, labeled specific binder 21, in this example labeled penicillin binder, and labeled multianalyte binder 22, in this example labeled beta-lactam (BL) binder. The penicillin binder 21 includes penicillin binding site 31, detectable label 32, for example gold particle, and protein A binding site 33. The BL binder 22 includes beta-lactam binding site 34, anti-BL binder binding site 35 and label 32.

The test zone 9 includes immobilized penicillin 38. In this embodiment, the beta-lactam ring of the immobilized penicillin is opened, depicted in this drawing as a break 24 in the ring, to reduce or eliminate the affinity of the beta-lactam binding site 34 of the BL binder 22. Binding site 39 on immobilized penicillin 38 is available to capture specific binder 21 unbound by penicillin from the sample. The test zone 4 includes immobilized representative beta-lactam 25 such as ceforanide. BL binder binding site 37 is available to capture BL binder 22 unbound by beta-lactam from the sample. The control zone 5 includes protein A 41. The control zone 5 also includes anti-BL binder 42. Protein A can capture penicillin binder 21 through attachment to the protein A site 33. As a result, protein A can capture both bound and unbound penicillin binder. If mixed together, Protein A 41 can also bind to anti-BL binder 42 at the control zone 5 to form an anti-BL binder-protein A complex 43 that may retain the ability to capture both penicillin binder 21 and BL binder 22. Anti-BL binder 42 can capture BL binder 22 unbound by beta-lactam from the sample or BL binder 22 bound by beta-lactam from the sample.

Figure 4:
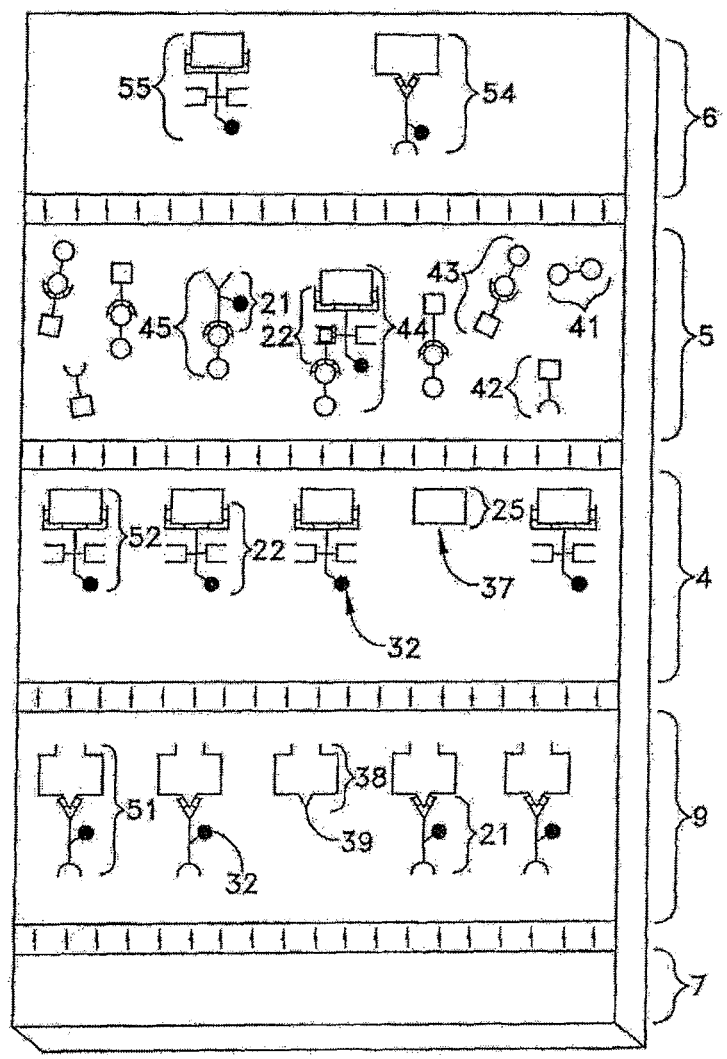
FIG. 4 is a schematic view of the test components after application of sample, wherein movement of fluid and formation of complexes is shown in an example of a test that is negative for both penicillin specifically and beta-lactams.

FIG. 4 shows a sample that is negative for both beta-lactams generally and the specific beta-lactam penicillin at the appropriate level of detection. After application of the sample, test components tyipcally flow out of binder application area 7. Penicillin binder 21, unbound by penicillin from the sample, can be captured by penicillin immobilized on the first test zone 9 to form a complex 51 that can be detected. Similarly, BL binder 22, unbound by beta-lactam from the test sample, can be captured by beta-lactam 25 immobilized on the second test zone 4 to form complex 52 that can be detected. Protein A 41 in control zone 5, whether complexed to anti-BL binder or alone, can capture both bound and unbound penicillin binder 21 that flow past the test zone 9 without being captured. In this figure complex 45 includes penicillin binder unbound by penicillin from the sample and captured at the control zone. The anti-BL binder 42, whether complexed to protein A, or alone, can capture both bound or unbound BL binder that flow past the test zone 4 without being captured, for example to form complex 44 in the control zone 5. In this figure some sample beta-lactam-BL binder complex 55 and sample penicillin-penicillin binder complex 54 are not captured and instead flow to the disposal pad 6. Not all labeled binder, whether or not bound by analyte from the sample, is necessarily captured at the test zones or control zone. Remaining label can flow to the disposal zone 6. The negative result can be determined, in the drawing, by counting the labels 32 in the control zone and test zones. In this example, the control zone 5 has two labels. The test zone 4 has four labels and the test zone 9 has four labels. Since the control zone has fewer labels than either of the test zones the test is negative for both penicillin and other beta-lactams. Although one beta-lactam from the sample was captured by BL binder 22 to form a complex that was captured 44 at the control zone 5, and one each of BL-binder and penicillin binder were bound by antibiotic to form complex 55 and complex 54 respectively, that flowed to the disposal zone 6, the semi-quantitative nature of the test is reflected in the negative result.

Figure 5:
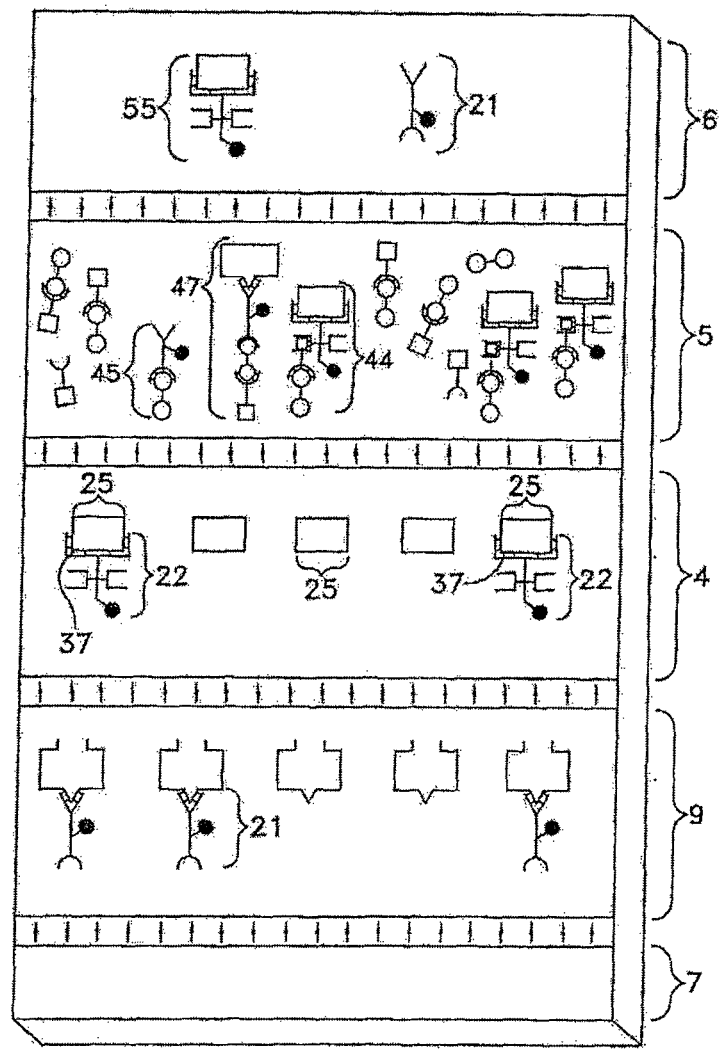
FIG. 5 is a schematic view of the test components after application of sample, wherein movement of fluid and formation of complexes is shown in an example of a test that is positive for both penicillin specifically and beta-lactams.

FIG. 5 shows a test that is positive for both penicillin specifically and beta-lactams. Three penicillin binders 21 are bound at test zone 9, two BL binders 22 are bound at test zone 4 and five binders are bound at control zone 5. Control zone 5 includes captured BL binder-label-sample beta-lactam complex 44, captured sample penicillin binder-label-penicillin complex 47 and captured unbound labeled penicillin binder complex 45. Disposal zone 6 includes penicillin binder 21 and BL binder-sample beta lactam complex 55, both of which slipped through uncaptured.

Figure 6:
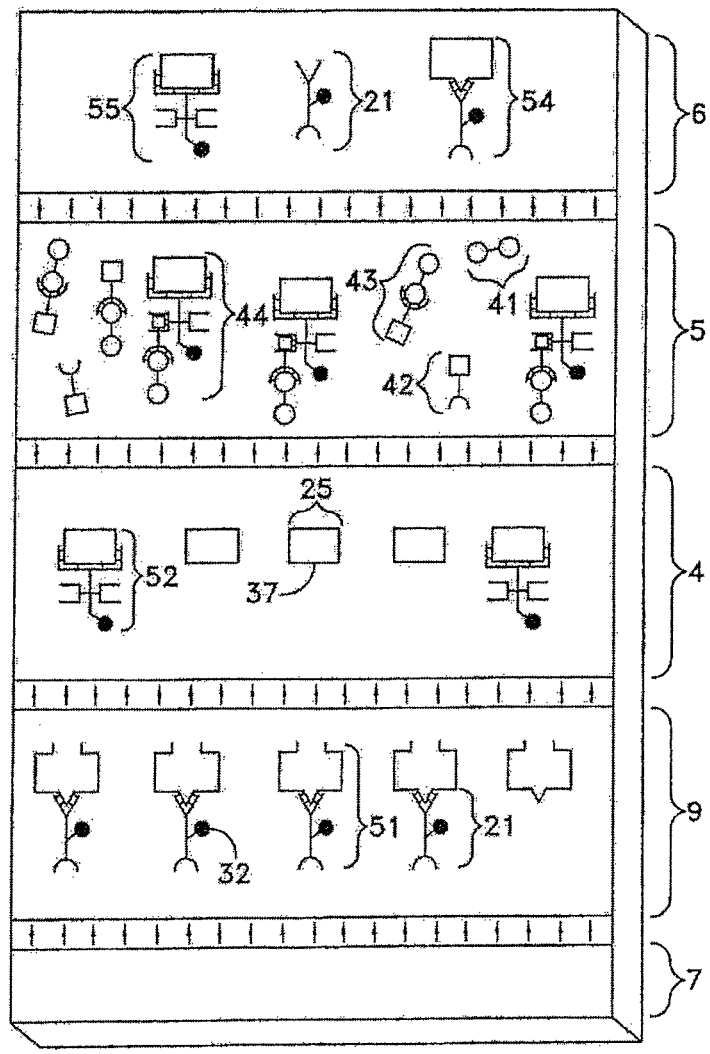
FIG. 6 is a schematic view of the test components after application of sample, wherein movement of fluid and formation of complexes is shown in an example of a test that is negative for penicillin specifically and positive for beta-lactams.

FIG. 6 shows a test that is positive for beta-lactams and negative for penicillin specifically. Three labels are captured at the control zone 5 and two labels are captured at test zone 4 while four labels are captured at test zone 9. Three labels are not captured and flow to the disposal zone 6.

Figure 7:
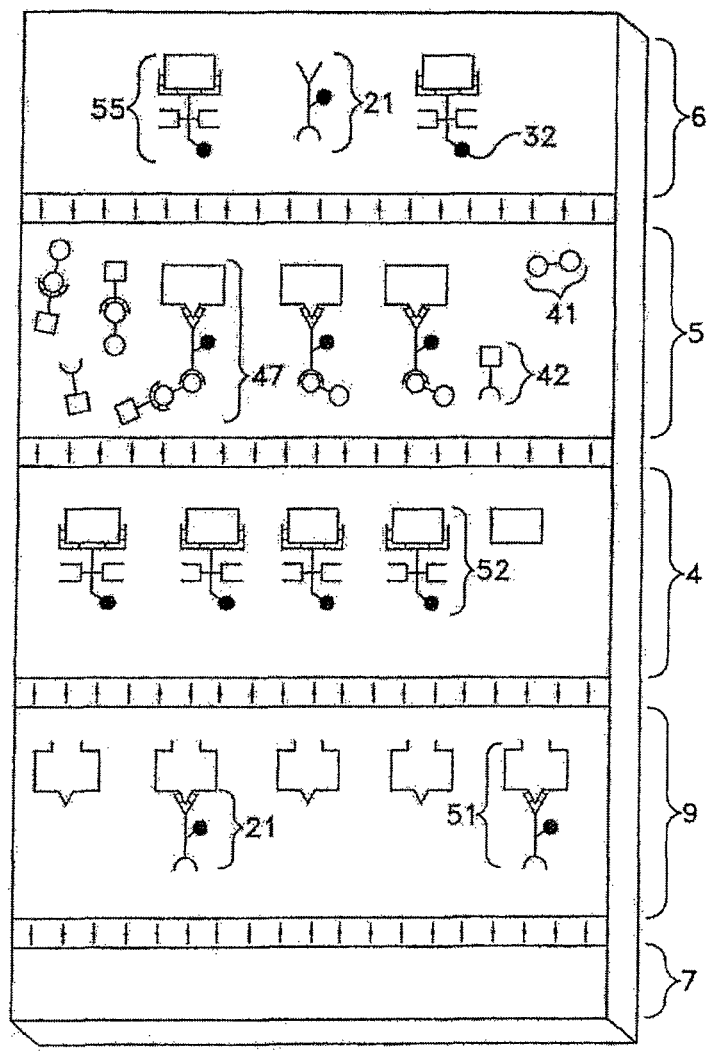
FIG. 7 is a schematic view of the test components after application of sample, wherein movement of fluid and formation of complexes is shown in an example of a test that is positive for penicillin specifically and negative for beta-lactams.

FIG. 7 shows a test that is negative for beta-lactams and positive for penicillin specifically. Two labels are captured at the test zone 9 and four labels are captured at the test zone 4 as compared to three labels captured at the control zone 5. Three labels are not captured and flow to the disposal zone 6.

It should be noted that the figures, particularly FIGS. 3-7, are highly simplified depictions designed to exemplify both the various mechanisms of capture, binding and affinity and test result interpretation. Although in these figures the mechanisms are largely described relative to detection of beta-lactams, including penicillin, the methods and assays described herein are not so limited.

In an example, a test zone capture agent can be, for example, an analyte, representative analyte, or analyte analogue. The capture agent at some point must be immobilized to the strip so that it is either removed from sample flow or is not solubilized by sample fluid flow. Immobilization on the strip, so that the capture agent is not solubilized by fluid flow, can be accomplished using a carrier protein such as bovine serum albumin (BSA), or other carrier protein well known in the art, for example ovalbumin (OVA) or keyhole limpet hemocyanin (KLH).

Each test zone capture agent may capture all or a portion of the binder, from what is known as the mobile phase, which is not already bound with sample analyte. A binder that is bound by analyte from the sample tends not to be captured at the test zone. Binders that are not captured at the test zone can be captured in the control zone or flow through to a disposal pad.

In an embodiment, a specific binder is a penicillin binder and a multianalyte binder is a BL binder. Both the penicillin binder and the BL binder can be detectably labeled, for example using gold particles. The labeled penicillin binder and labeled beta-lactam binder can be combined in a solution and applied, for example, by spraying, within or proximate to a pretreated POREX® (POREX is a registered trademark of Porex Technologies Corp, Georgia USA) sample pad in contact with a nitrocellulose membrane. The binders can also be combined with the sample in a container, such as a test tube, and added to the test strip with the sample. When exposed to a sample such as orange juice, the penicillin binder binds to penicillin in the orange juice and the BL binder binds to beta-lactams (including to some extent penicillin) in the orange juice to form complexes. Lateral capillary flow carries the complexes, and any uncomplexed labeled binders, to the test zone area of the strip.

In an embodiment using two binders, multiple test zones can be employed to capture the binders in separate zones. In an example in which penicillin binder and BL binder are used, the first test zone capture agent can include immobilized penicillin and the second test zone capture agent can include an immobilized different beta-lactam, such as ceforanide. In an embodiment in which the positions are reversed, the first test zone capture agent can include a representative beta-lactam and the second test zone capture agent can include penicillin. In the test zones, the capture agents can capture the binders that have not been previously bound by sample analyte. Such attachment at the test zone can generate a visible signal when a detectable label, such as gold or other label well known in the art, is used. Other particles that may be useful include, but are not limited to, colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles, colloidal metal ferrite particles, any of the above-mentioned colloidal particles coated with an organic or inorganic layer; protein or peptide molecules; liposomes; or organic polymer latex particles, such as polystyrene latex beads. Other labels may also be useful including, but not limited to, luminescent labels; fluorescent labels; or chemical labels, such as electroactive agents (e.g., ferrocyanide); enzymes; radioactive labels; or radiofrequency labels.

In an embodiment, two control zone capture agents are employed within the same control zone. The capture agents can each capture a different binder. In an embodiment in which a penicillin binder and a BL binder are both employed, protein A can be one control zone capture agent and an antibody to beta-lactam binder ("anti-BL binder") can be the other capture agent. In embodiments in which the anti-BL binder also has protein A binding affinity, such as when the anti-BL binder is rabbit antibody, the two control zone capture agents may become linked. In addition, either or both the protein A and anti-BL binder can be immobilized on the control zone using a carrier protein such as BSA.

In another embodiment, one control zone capture agent can be attached at the control zone and another control zone capture agent can be applied later for example by flowing to the control zone with the sample. For example, when the binders are a penicillin binder and a BL binder, the control zone can include protein A and anti-BL binder. Alternatively, the control zone can include protein A and the anti-BL binder can be bound to the BL binder and added to the strip with the BL binder such as on the sample pad. BL binder will retain beta-lactam binding activity after binding to anti-BL binder, but not after binding to a beta-lactam drug in the sample. In such an embodiment, the control zone capture agent is selected for its affinity to the anti-BL binder at a site not occupied by BL binder. Examples of such capture agents include Protein A, protein G, recombinant protein AG or other substances such as substances that bind, for example, to the constant region of an antibody.

In an embodiment, detectably labeled multianalyte binder ("labeled multianalyte binder) and detectably labeled specific binder ("labeled specific binder") are combined with unlabeled binders, such as unlabeled antibodies. The unlabeled antibodies are selected for their affinity to antibiotics to which the other binders, for example the multianalyte binder, are oversensitive. Such unlabeled binders compete with labeled multianalyte binders for a specific antibiotic and, thereby, reduce test sensitivity to the antibiotic/analyte to which the unlabeled binders have affinity. The unlabeled binders can have affinity for some or all of the analyte to which the labeled multianalyte binder has affinity. By including unlabeled binders with affinity for some, but not all, of the analytes to which a competing labeled binder has affinity, sensitivity of the test to those selected antibiotics/analytes will be reduced.

In some embodiments there is excess capture reagent in the control zone. Excess capture reagent will provide consistent control zone detection. In other control zone embodiments there is an excess of the general antibody binder, such as protein A, relative to the multianalyte binder capture agent, such as anti-BL binder, such as rabbit antireceptor. In a particular example using protein A and rabbit anti-BL binder, the control zone will have sufficient excess protein A available for capturing penicillin binder and binding the anti-BL binder.

In certain embodiments, in a negative sample the control zone will capture fewer labels as compared to any one of the test zones, in a positive sample for a single analyte or family, the control zone will capture more labels than one of the test zones and fewer labels than the other and, if positive for all analytes, each of the test zones will capture fewer labels as compared to the control zone.

Including multiple capture agents at the control zone, such as both protein A, or other general antibody binder, and specific antibody to a binder, such as anti-BL binder, provides the possibility of a test strip for detection of multiple analytes such as multiple antibiotics. For example, a test strip to detect sulfonamides, tetracyclines, amphenicols or macrolides, possibly combined on a test strip to detect beta-lactams, with a single control zone for comparison to multiple test zones for the different antibiotics. A control zone can have multiple specific antibodies to particular binders, multiple multianalyte binder antibodies, multiple antibody binding proteins or combinations thereof. Similarly, the control zone can include multiple antibodies of different host species and not necessarily include a general antibody binder. For example, if one binder is a mouse monoclonal antibody and another is a rabbit polyclonal antibody, the control zone can include an anti-mouse antibody and an anti-rabbit antibody.

In another embodiment, the assay can be in the form of a so-called sandwich assay using different types of binders, such as a combination of polyclonal and monoclonal antibodies or a combination of different species polyclonal antibodies. Tests to detect multiple analytes using a sandwich assay can include a plurality of labeled analyte binders that bind with different analytes. The test zone can include multiple immobilized binders for the analyte, for example with affinity to different regions of the analyte to which the labeled antibody has affinity. The control zone could include a combination of immobilized capture agents including, for example, combinations of anti-species antibodies for reactions to each of the different analyte binders. The control zone could also combine, depending on the binders used, a combination of general antibody binding protein, such as protein A, and an antibody for one of the binders to which protein A does not have adequate affinity, such as anti-mouse antibody. In such an embodiment, as with the other embodiments described herein in which the non-sandwich format is used, either the analyte binder can be labeled with a visible label or, in an embodiment, the label can require a further reaction such as when the label is an enzyme or substrate of an enzyme linked immunosorbent assay (ELISA).

In another embodiment, one type of binder, for example a labeled polyclonal antibody, can be used to detect a single analyte or a group of related analytes. One test zone and one control zone can be used to capture the labeled binder. The control zone can include multiple capture agents, each with different affinity to the binder, such as each with affinity to different parts of the binder. For example, if the labeled antibody is a rabbit polyclonal, the control zone capture agents can include, for example, an anti-rabbit antibody and an antibody binding protein such as protein A. By including different control zone capture agents, it may be possible to improve binder capture at the control zone and, thereby, improve the control zone signal.

In some embodiments BL binder is isolated directly from, for example, B.st., by immobilized ligand affinity chromatography techniques that are well known in the art.

The binder can also be expressed from other hosts by inserting into the host genome the sequence of the BL binder from B.st.

Another example of a useful multianalyte binder, that can be used in certain embodiments, includes a beta-lactam binding protein isolated from *Bacillus lichenformis*. Other possibly useful binders include macromolecules, such as monoclonal or polyclonal antibodies, hormone receptors and enzymes and synthetic receptors such as those generated through molecular imprinting of synthetic polymers or molecular imprinting inside dendrimers.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

We claim:

1. A lateral flow assay system for detecting one or more analytes in a solution, the system comprising:

(a) a buffer comprising a carrier protein and a base configured to increase the pH of a low pH sample from a pH between about 2 and about 5 to an optimal pH of about 7, wherein the combination of the low pH sample and the buffer forms the solution;

(b) a binder configured for generating a detectable signal, wherein the binder being adapted to combine with an analyte from the solution to form a binder-analyte complex; and (c) a test strip configured to allow a test solution to flow, wherein the test solution contains either or both a binder and a binder-analyte complex, the test strip comprising:

(i) a test zone having immobilized thereon a test zone capture agent that, when the binder has not formed a binder-analyte complex, captures the binder, (ii) a control zone having at least one control zone capture agent adapted to capture the binder, whether or not the binder has formed a binder-analyte complex, and wherein capture of the binder at either the test zone or control zone results in a detectable signal and wherein a greater signal in the control zone as compared to the test zone indicates a positive result.

2. The system of claim 1, wherein the low pH sample has a pH of about 3.

3. The system of claim 1, wherein the low pH sample is a citrus juice.

4. The system of claim 3, wherein the citrus juice is selected from the group consisting of lemon juice, lime juice, grapefruit juice, and orange juice.

5. The system of claim 1, wherein the carrier protein is bovine serum albumin.

6. The system of claim 1, wherein the base is sodium bicarbonate.

7. The system of claim 6, wherein the sodium bicarbonate is about 0.7M.

8. The system of claim 1, wherein the analyte includes an antibiotic.

9. The system of claim 8, wherein the antibiotic comprises oxytetracycline.

10. The system of claim 8, wherein the antibiotic comprises streptomycin.

* * * * *